United States Patent [19]

Ribalta Baro et al.

[11] Patent Number: 5,082,969
[45] Date of Patent: Jan. 21, 1992

[54] INDUSTRIAL PROCESS FOR OBTAINING AN ARYLOXYPROPANOLAMINE

[75] Inventors: Josep M. Ribalta Baro, Esplugues de Llobregat; Gloria Oranias Olsina; Julio Campon Pardo, both of Barcelona, all of Spain

[73] Assignee: Esteve Quimica, S.A., Barcelona, Spain

[21] Appl. No.: 525,410

[22] Filed: May 16, 1990

[30] Foreign Application Priority Data

May 26, 1989 [ES] Spain ................... 89 01774

[51] Int. Cl.$^5$ ............................................. C07C 209/14
[52] U.S. Cl. ...................................................... 564/349
[58] Field of Search .......................................... 564/349

[56] References Cited

U.S. PATENT DOCUMENTS

| | | | |
|---|---|---|---|
| 3,780,081 | 12/1973 | Le Count et al. | 564/349 X |
| 3,998,790 | 12/1976 | Brandstrom et al. | 564/349 |
| 4,258,062 | 3/1981 | Jonas et al. | 564/349 X |
| 4,396,629 | 8/1983 | Phillion | 564/349 X |
| 4,515,814 | 5/1985 | Wick et al. | 564/349 X |
| 4,760,182 | 7/1988 | Ippolito et al. | 564/349 |

Primary Examiner—Richard L. Raymond
Attorney, Agent, or Firm—Ladas & Parry

[57] ABSTRACT

Industrial process for obtaining an aryloxypropanolamine of chemical name 1-[4-(2-methoxyethyl)phenoxy]-3-[(1-methylethyl)amino]-2-propanol, characterized in that it comprises the following operating phases. By reacting 4-(2-methoxyethyl)phenol with epichlorohydrin in an alkaline aqueous medium at temperatures of between 0° and 25° C. a crude reaction product composed to the extent of 75-80% of 3-[4-(2-methoxyethyl)phenoxy]-1,2-epoxypropane and to the extent of 15-20% of 1-[4-(2-methoxyethyl)phenoxy]-3-chloro-2-propanol is obtained, after the appropriate extractions and washings, both compounds being suitable for reacting with isopropylamine in an aqueous medium and at temperatures ranging between 0° and 30° C. to obtain the desired aryloxypropanolamine of formula I.

3 Claims, No Drawings

INDUSTRIAL PROCESS FOR OBTAINING AN ARYLOXYPROPANOLAMINE

The present invention relates to an industrial process for obtaining an aryloxypropanolamine of chemical name 1-[4-(2-methoxyethyl)phenoxy]-3-[(1-methylethyl)amino]-2-propanol of formula I, which is isolated in the form of the L-tartrate.

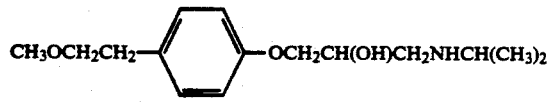

This product owes its commercial interest to its pharmacological action as a cardiac β-blocker, and is therefore applicable for the treatment of cardiovascular diseases.

PRIOR ART

The process of obtaining the product of formula I is described for the first time by A. E. Brandstrom et al. (German Patent 2,106,209 or its equivalent U.S. Pat. No. 3,873,600), starting from the intermediate 3-[4-(2-methoxyethyl)phenoxy]-1,2-epoxypropane of formula II

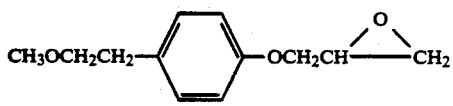

condensing it in an alcoholic medium with isopropylamine, using drastic conditions of temperature and pressure in an autoclave and for long reaction times.

In Japanese Patent Kokai Tokkyo Koho JP 57/169,448 (Chemical Abstracts 98:106952a or the equivalent Spanish Patent 510,956), the intermediate of formula II is also used, reacting it with an alkaline or Al, Si or Mg salt of isopropylamine, which must previously be prepared from expensive raw materials such as triethylaluminium.

A more advantageous process is that described in European Patent Application 50,885 by C. Giordano, in which the epoxide of formula II is treated with a large excess of isopropylamine in the presence of a catalyst which is a Lewis acid.

All this has led us to develop a new process, the subject of the present invention, which allows us to obtain a product of great purity by means of a straightforward process which has high yields.

DESCRIPTION OF THE INVENTION

According to the process described in the present invention the compound of formula I is prepared by means of the following sequence of reactions:

Firstly the 4-(2-methoxyethyl)phenol of formula III:

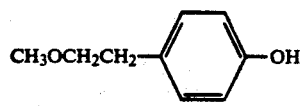

is reacted with epichlorohydrin in an alkaline aqueous medium at temperatures of between 0° and 25° C., to give rise, after the appropriate extractions and washings, to a crude reaction product composed to the extent of 75-80% of the epoxide of formula II

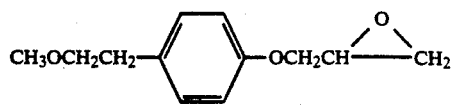

and to the extent of 15-20% of the chlorohydrin of formula IV, which corresponds to 1-[4-(2-methoxyethyl)phenoxy]-3-chloro-2-propanol.

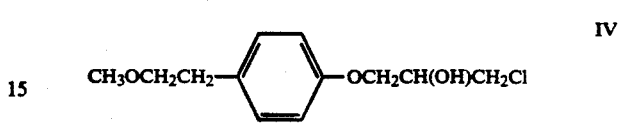

The second phase of the process consists in treating the mixture of epoxide and chlorohydrin in an aqueous medium with isopropylamine at moderate temperatures ranging between 0 and 30° C., to obtain in this manner, from the mixture of both synthetic precursors, the aryloxypropanolamine of formula I. These very straightforward operating conditions present notable advantages with respect to other processes which require organic solvents, special installations such as autoclaves in order to work at high pressures and temperatures, or even require the use of catalysts.

The base is isolated by extraction with a suitable solvent such as toluene, xylene, ethyl acetate or a chlorinated solvent, which is removed afterwards by distillation, and the L-tartrate is prepared in acetone, the desired product being isolated by filtration.

DESCRIPTION OF ILLUSTRATIVE EMBODIMENTS

In order to facilitate understanding of the process which is the subject of the present invention, examples of the different phases of the process are supplied, but should not be considered as limiting.

EXAMPLE 1

To obtain 3-4-(2-methoxyethyl)phenoxy1-1,2-epoxypropane.

25 kg of previously melted 4-(2-methoxyethyl)phenol are added to a solution of 7.4 kg of sodium hydroxide in 160 l of water, maintaining the temperature between 10° and 15° C. 30 kg of epichlorohydrin are added to the suspension of sodium phenolate at the said temperature.

The mixture is stirred for about 15-20 hours at 20°-25° C. The organic phase is decanted and washed twice with 25 l of water. The aqueous extracts are dried, and the excess epichlorohydrin is distilled from the organic phase, 31.5 kg (92%) of a slightly yellowish liquid which contains 75-80% epoxide and 15-20% of the chlorohydrin being obtained in this manner.

This material is of sufficient quality to be used as such in the following reaction step.

EXAMPLE 2

To obtain 1-4-(2-methoxyethyl)phenoxy]-3-[(1-methylethyl)amino]-2-propanol.

31 kg of crude epoxide from the previous step are added to a solution of 132 kg of isopropylamine in 56 l of water at 10°-15° C. The mixture is heated to 30° C. and kept at this temperature for 4 h. The excess isopropylamine is distilled, and 50 l of toluene are added. The mixture is stirred for 10 minutes and decanted. The organic phase is washed twice with 50 l of water. The aqueous extracts are dried, and the organic phase is concentrated by distilling the toluene, which can be recycled.

In this manner 35 kg (88%) of crude base are obtained, which are dissolved in 60 l of acetone for the preparation of the corresponding L-tartrate.

If it is left to stand the concentrated base crystallizes slowly, and by recrystallization with n-heptane a white product of m.p. 47° C. is obtained.

IR (Nujol): Characteristic bands at 3320, 1630–1600, 1530, 1250, 1160, 1020, 900 and 820 cm⁻¹.

EXAMPLE 3

To obtain the L-tartrate of 1-[4-(2-methoxyethyl)phenoxy]-3-[(1-methylethyl)amino-2-propanol.

A solution of 5.6 kg of L-tartaric acid in 150 l of acetone is added at ambient temperature to a solution of 20 kg of 1-[4-(2-methoxyethyl)phenoxy]-3-[(1-methylethyl)amino]-2-propanol in 40 l of acetone. Shortly after completion of the addition a rapid precipitation of the product starts, it being necessary to maintain energetic stirring during the process. Once precipitation is finished, stirring is maintained for one hour at 5°–10° C., and the precipitate is filtered off and washed with acetone.

In this manner 24.6 kg (96%) of a white product of high purity are obtained, of m.p.: 121°–122° C.

[α]: +8.6°

IR (KBr): Characteristic bands at 3060-2840, 1600, 1540, 1410-1390, 1260, 1120 and 830 cm⁻¹.

We claim:

1. Industrial process for obtaining an aryloxypropanolamine of chemical name 1-[4-(2-methoxyethyl)-phenoxy]-3-[(1-methylethyl)amino]-2-propanol of Formula I:

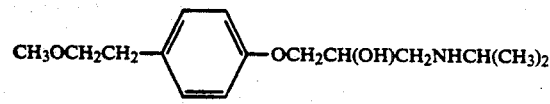

comprising:

1) reacting 4-(2-methoxyethyl)phenol of Formula III

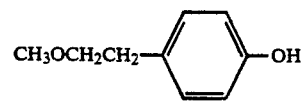

with epichlorohydrin in an alkaline aqueous medium at temperatures of between 0° and 25° C.;

2) obtaining a crude reaction product composed of 75–80% of 3-[4-(2-methoxyethyl)phenoxy]-1,2-epoxypropane of Formula II:

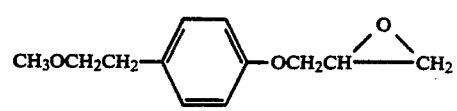

and 15–20% of 1-[4-(2-methoxyethyl)-phenoxy-3-chloro-2-propanol of Formula IV:

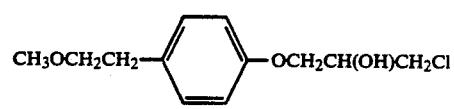

3) extracting and washing the reaction products of Step 2 and;

4) reacting either the compound of formula II or the compound of formula IV or a mixture thereof with isopropylamine in an aqueous medium at temperatures ranging between 0° and 30° C. to obtain the desired aryloxypropanolamine of Formula I.

2. Industrial process for obtaining an aryloxypropanolamine, according to claim 1, wherein compound I is isolated from the reaction medium by extraction with a suitable solvent selected from the group consisting of toluene, xylene, ethyl acetate and a chlorinated solvent, and after said extraction said solvent is removed by distillation.

3. Industrial process for obtaining an aryloxypropanolamine, according to claim 1, wherein the L-tartrate of the aryloxypropanolamine of formula I is prepared in an acetone medium, the product being isolated by filtration.

* * * * *